United States Patent [19]

Gula et al.

[11] Patent Number: 5,478,953
[45] Date of Patent: Dec. 26, 1995

[54] PROCESS FOR THE PREPARATION OF CIS-SYN-CIS-4,4'(5')-[DI-T-BUTYLDICYCLOHEXANO]-18-CROWN-6

[75] Inventors: Michael J. Gula, Chicago, Ill.; Richard A. Bartsch, Lubbock, Tex.

[73] Assignee: Eichrom Industries, Inc., Darien, Ill.

[21] Appl. No.: 333,783

[22] Filed: Nov. 3, 1994

[51] Int. Cl.$^6$ .................................................. C07D 323/00
[52] U.S. Cl. .................................................................. 549/349
[58] Field of Search ............................................. 549/349

[56] References Cited

U.S. PATENT DOCUMENTS

| | | | |
|---|---|---|---|
| 3,687,978 | 8/1972 | Pedersen | 549/349 |
| 5,082,955 | 1/1992 | Lemaire et al. | 549/349 |
| 5,100,585 | 5/1992 | Horivitz et al. | 252/631 |
| 5,110,474 | 5/1992 | Horivitz et al. | 210/635 |
| 5,346,618 | 9/1994 | Horivitz et al. | 210/198.2 |

Primary Examiner—Bernard Dentz
Attorney, Agent, or Firm—Welsh & Katz, Ltd.

[57] ABSTRACT

A process for preparing 4,4'(5')-[di-t-butyldicyclohexano]-18-crown-6 containing an enhanced amount of an isomer that extracts strontium ions from aqueous solution is disclosed. According to the process, an anhydrous reaction mixture is prepared containing 4,4'(5')-[di-t-butyldibenzo]-18-crown-6 as substrate dissolved in a $C_2$–$C_6$ alcohol-containing solvent that can also contain benzene, toluene or xylene, a $C_2$–$C_6$ carboxylic acid or anhydride and a 5 percent of rhodium on alumina particle catalyst. The resulting reaction medium is hydrogenated at about 200–1000 psi, at a temperature of about 35°–120° C. for a time period sufficient to reduce at least 90 percent of the substrate.

11 Claims, No Drawings

PROCESS FOR THE PREPARATION OF CIS-SYN-CIS-4,4' (5')-[DI-T-BUTYLDICYCLOHEXANO]-18-CROWN-6

TECHNICAL FIELD

The present invention relates to the preparation of a crown ether (macrocyclic polyether) that selectively extracts strontium ions from strongly acidic nitric acid solutions, and more particularly to the preparation of 4,4'(5')-[ di-t-butyldicyclohexano]-18-crown-6 having an enhanced proportion of the cis-syn-cis isomer.

BACKGROUND ART

U.S. Pat. Nos. 5,100,585, 5,110,474 and 5,346,618, whose disclosures are incorporated by reference, teach the use of several crown ether compounds in extracting various ions from 1–6 molar nitric acid solutions under various extraction conditions, including dispersal of the crown ether on an inert resin substrate material. Of the several crown ethers discussed, 4,4'(5')-[ di-t-butyldicyclohexano]-18-crown-6 (Dt-BuCH18C6) was shown to be particularly effective at extracting strontium ions from nitric acid solutions.

This crown ether, Dt-BuCH18C6 (Compound 2), is prepared by the catalytic hydrogenation of the corresponding 4,4'(5')-[di-t-butyldibenzo]- 18-crown-6 (Compound 1), as is shown generally below in Scheme 1.

Several isomers can form during the hydrogenation reaction. Some of those isomers do not effectively coordinate (complex) with strontium ions ($Sr^{+2}$), whereas one or more isomers coordinate with strontium ions very well. Coordination (complexation) between the crown ether and strontium ions is the first step in extraction of strontium ions from an aqueous medium into an organic medium containing the macrocyclic ether. Such extraction provides a useful measure of coordination or complexation ability of the crown ether.

Of the isomers of Compound 2 formed during the catalytic hydrogenation shown in Scheme 1, one isomer, believed to have both cyclohexane rings cis-fused in a syn-configuration (cis-syn-cis; Compound 2b) is an excellent extractant (coordinator) of $Sr^{+2}$ ions, whereas isomers in which the cyclohexane rings are thought to be trans-fused to the crown ether ring (e.g., Compound 2a; trans-anti-trans) do not extract (coordinate with) strontium ions in a model extraction system.

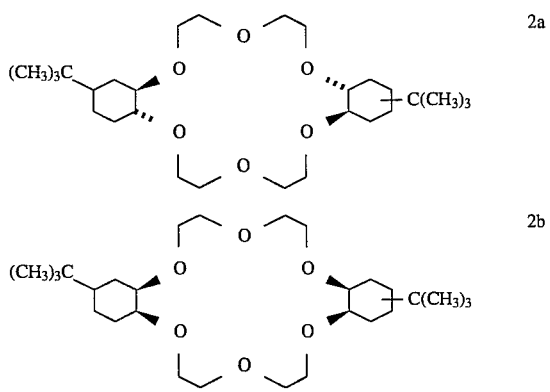

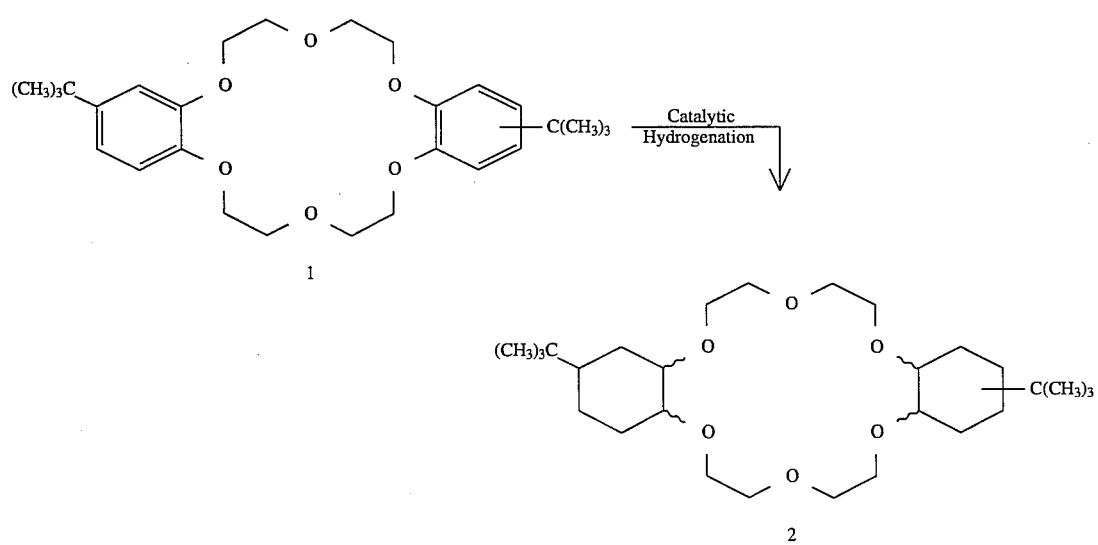

Scheme 1

In the above compound depictions, wavy lines are used to indicate that the depicted bond can be above or below the plane of the page. Darkened wedge-shaped lines are used to indicate bonds that extend above the plane of the page, whereas dashed wedge-shaped lines are used to indicate bonds that extend below the plane of the page.

Put in numerical terms, the distribution ratio, D, between an aqueous 1M nitric acid solution containing tracer amounts strontium ions and three volumes of n-octanol containing a trans-fused crown ether at 0.5M is zero, whereas the ratio for the cis-syn-cis isomer is about 5–6. These studies are discussed in part in U.S. Pat. No. 5,100,585.

Effective extraction of strontium ions from nitric acid solutions of dissolved waste sludge of nuclear reactors or other media does not require absolute purity of the crown ether. A distribution ratio, D-value, of 2 or more, and preferably about 3 or greater provides adequate separations.

Achieving an adequate quantity of the cis-syn-cis isomer of Compound 2; i.e., Compound 2b, in the crown ether has been costly and problematic. Thus, reduction levels of starting material, Compound 1, have been erratic and are often in the range of about 10 to about 65 percent, with some preparations having almost none of the desired isomer for no apparent reason. When the desired cis-syn-cis isomer is present, that material is typically separated by column chromatography on alumina, which is useful but adds to the cost of the extractant.

It would therefore be beneficial if a process were available for consistently preparing an enhanced yield of the desired Compound 2 that contained an enhanced amount of the desired cis-syn-cis isomer, Compound 2b. It would also be beneficial if such a process could produce a product with sufficient isomeric content of Compound 2b so that material could be utilized without purification except for separation from the catalyst. The present invention provides such processes.

BRIEF SUMMARY OF THE INVENTION

The present invention contemplates a process for preparing excellent yields of 4,4'(5')-[ di-t-butyldicyclohexano]-18-crown-6 (Dt-BuCH18C6) as product containing at least one-third of the cis-syn-cis isomer. More preferably at least one-half of the product is the desired isomer, and most preferably about two-thirds to about four-fifths of the product is that desired isomer.

In accordance with that process, an anhydrous reaction mixture is formed that consists essentially of (i) 4,4'(5')-[di-t-butyldibenzo]- 18-crown-6 as substrate, dissolved in (ii) a solvent that is a $C_2$-$C_6$ alkyl alcohol that contains zero to 2 parts by weight benzene, toluene or xylene per part of alcohol, (iii) a heterogeneous catalyst that contains about 5 weight percent of rhodium on aluminum particles, and (iv) a $C_2$- $C_6$ carboxylic acid or carboxylic acid anhydride. The substrate is free of oxyethylene hydroxylic and oxyethylene phenolic impurities. The weight ratio of the substrate to the catalyst is about 50 to about 5:1, and the weight ratio of catalyst to the carboxylic acid or carboxylic anhydride is about 0.5:1 to about 10:1.

The reaction mixture so formed is hydrogenated at a pressure of about 200 to about 1000 psi at a temperature of about 35° C. to about 120° C. for a time period sufficient to reduce at least 90 percent of the substrate, e.g., of about 4 to about 24 hours.

In preferred practice, the $C_2$–$C_6$ alcohol solvent is n-butanol, the pressure used is about 400 to about 800 psi, the temperature is about 60° to about 65° C., the time period of hydrogenation is about 8 to about 24 hours, and the $C_2$–$C_6$ carboxylic acid or carboxylic anhydride is acetic acid or acetic anhydride.

The catalyst is preferably a moderately active rhodium on alumina particle material. More preferably, the catalyst is about a 1:2 parts by weight mixture of that moderately active catalyst and a more active catalyst to provide a catalyst whose BET surface area is in the range of about 95 to about 120 $m^2$/g.

The present invention has several benefits and advantages.

One benefit is that its use provides consistent high consumption of the substrate starting material, Compound 1, typically ranging from about 90 to about 100 percent.

Another benefit is that the yield of product, Compound 2, is also high so that the costly starting material is not wasted.

An advantage of the invention is that its use provides consistent yields of the desired cis-syn-cis isomer, which is the excellent strontium ion extractant, Compound 2b in excess of one-third to about 80 percent of the product formed.

Another advantage of the invention is that the hydrogenation product usually does not need further purification, as where it is utilized dispersed on an inert resin substrate material in a so-called SREX column as discussed in U.S. Pat. Nos. 5,110,474 and 5,346,618.

Still further benefits and advantages of the present invention will be apparent to a worker of ordinary skill from the disclosure that follows.

DETAILED DESCRIPTION OF THE INVENTION

The usefulness of an extractant is measured by the distribution ratio, D, of an extracted material between the extracting medium and the medium from which the desired material is extracted. The D-values are measured under predetermined, standardized conditions discussed in Example 1 hereinafter.

For strontium ion, $Sr^{+2}$ in an aqueous 1M nitric acid solution, the maximum D-value found for an isomer of Compound 2 is about 6 under those specified standard conditions. According to Horowitz et al., *Solvent Ext. Ion Exch.*, 9(1):1–25 (1991) the cis-syn-cis isomer, Compound 2b, provides that D-value. A transisomer such as Compound 2a provides a D-value of zero.

Pederson, *Org. Syn.*, Collective Volume VI, Wiley, New York (1988) pp. 395–400, discloses a procedure for converting dibenzo-18-crown-6 to dicyclohexano-18-crown-6 by high pressure hydrogenation. That procedure utilizes a five percent ruthenium on alumina catalyst, a temperature of 100° C., a pressure of 1000 psi and a hydrogenation time of 22 hours. Use of that process by the inventors here provided a 95 percent yield of the dicyclohexano-18-crown-6. However, less than 10 percent yield of Compound 2 was obtained when Compound 1 was used instead of the dibenzo-18-crown-6. Clearly, an improved process was required.

The present invention not only provides a process by which high yields of reduction product, Compound 2, are provided, but also provides a process by which the isomer of Compound 2 that provides excellent extraction D-values is formed in about 33.3 to about 80 percent yield of the reduction product, Compound 2. Those high yields of Compound 2, and its desired good extractant, believed to be Compound 2b, are surprising in themselves, and are also surprising in the consistency for this previously unpredictable reaction.

Thus, in accordance with this process, an anhydrous reaction mixture is formed that consists essentially of (i) 4,4'(5')-[di-t-butyldibenzo] -18-crown-6 as substrate, dissolved in (ii) a solvent that is a $C_2$–$C_6$ alkyl alcohol that contains zero to 2 parts by weight benzene, toluene or xylene per part alcohol, (iii) a heterogeneous catalyst that contains about 5 weight percent rhodium on aluminum particles, and (iv) a $C_2$–$C_6$ carboxylic acid or carboxylic acid anhydride. The substrate is free of oxyethylene hydroxylic and oxyethylene phenolic impurities. The weight ratio of the substrate to the catalyst is about 50 to about 5:1, and the weight ratio of catalyst to the carboxylic acid or carboxylic anhydride is about 0.5:1 to about 10:1.

The reaction mixture so formed is hydrogenated at a pressure of about 200 to about 1000 psi at a temperature of about 35° C. to about 120° C. for a time period sufficient to reduce at least 90 percent of the substrate, e.g., of about 4 to about 24 hours.

The reaction mixture is anhydrous as is the catalytic hydrogenation of that reaction mixture. Thus, the $C_2$–$C_6$ alcohol is dried and distilled under dry conditions prior to use, as is the aromatic hydrocarbon when present. The catalyst is also dried prior to use as by heating to a temperature of about 110°–120° C. under reduced pressure (about 0.5 mm) for about four hours prior to use. The starting material can also be freed from water prior to use by azeotropic distillation with the aromatic hydrocarbon solvent.

This requirement for anhydrous reaction conditions was unexpected for several reasons. First, the inventors and their co-workers at first found no predictable effect of the water content of the catalyst upon the reaction in initial studies. In addition, there are several literature reports of benzenoid ring reductions using a rhodium catalyst that are carried out in water as solvent. See, M. Freifelder, *Practical Catalytic Hydrogenation*, Wiley-Interscience, New York, (1971), pp. 13–15 and 68.

The substrate, Compound 1, must also be purified, and particularly be free from oxyethylene phenolic and other oxyethylene hydroxylic impurities that can occur from the use of incompletely cyclized material. These and other impurities can be identified by nuclear magnetic resonance (NMR) and infrared (IR) analyses at levels down to about 1 percent of the substrate. The $^1$H-NMR peaks in the region of 3.5– 4.5 δ are particularly good indicators of purity.

The substrate, Compound 1, is prepared as discussed in Pederson, *Org. Syn.*, Collective Vol. VI, Wiley, New York (1988) pp. 395–400, by substituting 4-t-butylcatechol in reaction with bis( 2-chloroethyl)ether in n-butanol in the presence of an excess of sodium hydroxide under reflux. Once the reaction is completed, the excess sodium hydroxide is neutralized with aqueous HCl, followed by distillation of much of the n-butanol, addition of water, cooling, addition of acetone to precipitate the substrate, filtration of the precipitate, washing with water and acetone, and filtration.

Exemplary $C_2$–$C_6$ alcohols include ethanol, propanol, isopropyl alcohol, n-butanol, 2-butanol, pentanol, 2-pentanol, hexanol and the like. n-Butanol is particularly preferred.

The alcohol solvent is dried by distillation prior to use. In an exemplary distillation of n-butanol, the first 10–15 percent of the distillate is discarded, the next about 80–85 percent is collected in a dry container and kept under an atmosphere of dry nitrogen prior to use. The remaining alcohol is discarded. Other $C_2$–$C_6$ alcohols are used similarly.

An anhydrous aromatic hydrocarbon such as benzene, toluene or xylene can also be present as part of the solvent, and preferably is present. That aromatic hydrocarbon can be present at zero to about 2 parts by weight per part $C_2$–$C_6$ alcohol. Usual quantities range from about one-third part to about one part by weight per part alcohol, so that the aromatic hydrocarbon constitutes about 25 to about 50 weight percent of the solvent.

The amount of total solvent does not appear to be critical so long as the reaction mixture remains fluid at ambient room temperature before and after hydrogenation. Solvent to substrate weight ratios of about 5 to about 15:1 are useful, with a weight ratio of about 6 to about 10:1 being preferred.

The $C_2$–$C_6$ carboxylic acid or carboxylic anhydride can be any one of materials such as acetic acid or acetic anhydride, butyric acid or butyric anhydride, isobutyric acid or anhydride, pentanoic acid or anhydride, isovaleric acid or anhydride, hexanoic acid or anhydride, and the like. Acetic acid is particularly preferred. Strong acids such as sulfuric and p-toluenesulfonic acids are not useful here.

The $C_2$–$C_6$ carboxylic acid or anhydride (that reacts in situ to form at least one mole of carboxylic acid) appears to function at least as an accelerant for the reaction. It also appears as though the presence of the carboxylic acid affects the isomeric distribution in the product. The use of a strong acid such as sulfuric or p-toluenesulfonic acids caused about 95 to 100 percent conversion of starting materials with D-values for the product being about 1 or less, or a poor conversion of sbustrate to form a mixture that was not readily worked with.

The use of acids, particularly strong acids, such as sulfuric or p-toluenesulfonic acids as accelerators for some reductions is known. However, those reductions typically involved amine-containing compounds or other structures very different from those involved here. In addition, the acids normally used were strong or relatively strong acids having a $pK_a$ value below 3, such as sulfuric, perchloric, hydrochloric or trifluoroacetic, or long-chain, surfactant-type acids, such as palmitic and oleic acids, and the catalysts were other than rhodium. See, Freifelder, *Practical Catalytic Hydrogenation*, Wiley-Interscience, New York, (1971) pp. 66–68. Those prior uses of other acids in other substrate and catalyst systems provided no hint of stereochemical control of the products due to the presence of a small amount of a weak carboxylic acid; i.e., a carboxylic acid having a $pK_a$ of about 4 to about 5.

It is to be understood that when a $C_2$–$C_6$ carboxylic acid anhydride is in the presence of a $C_2$–$C_6$ alcohol as solvent that the two react to form a $C_2$–$C_6$ carboxylic ester of the $C_2$–$C_6$ alcohol, liberating one mole of carboxylic acid per mole of alcohol reacted. In addition, if water is present, the carboxylic anhydride can react with the water to form two moles of carboxylic acid, although most of the reaction is with the alcohol because of its higher concentration.

The carboxylic anhydride typically is not present at a time after completion of the hydrogenation. However, the presence of carboxylic anhydride can be inferred from the presence of $C_2$–$C_6$ carboxylic ester of the $C_2$–$C_6$ alcohol solvent plus an amount of free carboxylic acid. The amount of the ester present because of reaction of the solvent and anhydride is relatively minor, constituting only a few percent whose maximal amount is governed by the ratio of alcoholic solvent to carboxylic acid anhydride, and thus does not materially change the fundamental character of the reaction mixture.

The catalyst used for the catalytic hydrogenation contains about 5 weight percent of rhodium on alumina particles. A similar catalyst containing about 15 weight of rhodium was less effective, causing a slower reaction and incomplete conversion.

Catalyst activity can in part be a function of the size and therefore surface area of the support particles, with smaller particle size and concomitant increased surface area providing enhanced activity. It is also preferred that the catalyst be reduced, dry and not be supplied in a form containing water.

A preferred catalyst is sold under the designation AP-8 alumina powder, reduced, dry (C3919) by Engelhard Corp. of Seneca, S.C. This material typically contains about 4.8–5.2 weight percent rhodium, loses a maximum of two percent weight on heating at 120° C. for 16 hours and has a BET surface area that is typically about 105 m$^2$/g, with a range of about 95 to about 115 m$^2$/g. This catalyst can be used by itself. This is a moderately active catalyst.

It is preferred to use up to about 80 weight percent of the total catalyst of a more active catalyst having usual properties that are the same as those above, but whose BET surface area is typically about 110 m$^2$/g with a range of about 100 to about 120 m$^2$/g. This catalyst is an experimental, highly active catalyst available from Engelhard under the designation APX1 alumina powder, reduced, dry (C4150). This active catalyst can be used alone, but when so used, does not provide a consistently desirable D-value to the product. Better consistency in the product is obtained by use of a mixture of both catalysts.

Although up to about 80 weight percent of the total catalyst can be catalyst APX-1, it is more preferred to use the two catalysts mixed at about two parts highly active (APX-1) to moderately active (AP-8) catalyst.

The substrate, Compound 1, is present at a weight ratio to the catalyst of about 50 to about 5:1, more preferably at about 20 to about 10:1, and most preferably at about 10:1. This relatively low ratio of substrate to catalyst is used to speed the reaction, and higher weight ratios can be used, but are less preferred.

The weight ratio of catalyst to $C_2$–$C_6$ carboxylic acid or $C_2$–$C_6$ carboxylic acid anhydride is about 0.5:1 to about 10:1, based on the weight of acetic acid, and more preferably at about the same weight as the catalyst. Put differently, the carboxylic acid or anhydride is present at about twice to about one-tenth of the weight of the catalyst. More preferably, that weight ratio is about 1:1. When an acid other than acetic acid is used, the amount used is based on the weight of acetic acid so that a greater weight of a higher molecular weight acid is used. The amount of anhydride is preferably calculated as if one mole of acid were provided, so that about twice the amount of an anhydride is used as compared to acid; i.e., twice the weight of acid less one mole of water.

The most preferred weight ratio of substrate to catalyst to carboxylic acid or anhydride is about 10: about 1: about 1.

It has been found that whereas impure Compound 1 is soluble in n-butanol and other alcoholic solvents, the highly purified material free of oxyethylene hydroxylic or oxyethylene phenolic impurities is poorly soluble. Sufficient solubility is present for complete hydrogenation to occur because the product is more soluble in an alcohol-containing solvent so that as substrate is reduced, more dissolves, with the product remaining in solution. Highly purified Compound 1 is quite soluble in each of the before-mentioned aromatic hydrocarbons, particularly benzene and toluene. Each of the three aromatic hydrocarbons forms an azeotrope with water.

Thus, in preferred practice, purified substrate Compound 1 free of oxyethylene hydroxylic and oxyethylene phenolic impurities is dissolved in an excess amount of aromatic hydrocarbon, and the solution is heated to reflux using a Dean-Stark trap or similar apparatus to azeotropically dry the substrate. Once the azeotrope stops distilling, the volume of solution is reduced to provide the desired amount of dry aromatic hydrocarbon by simple distillation of that aromatic hydrocarbon or on a rotary evaporator, thereby providing an anhydrous solution of substrate Compound 1. Preferably, concentration of the dried solution is continued until a saturated solution is formed; i.e., crystal formation begins.

The aromatic hydrocarbon can be reduced during hydrogenation of the substrate to form cyclohexane or a corresponding methylated cyclohexane. This procedure uses more hydrogen than is needed to form the product, Compound 2, but is not otherwise deleterious to the process.

The anhydrous reaction mixture preferably formed by mixing each of the substrate solution, alcohol-containing solvent, carboxylic acid or carboxylic anhydride and catalyst is then hydrogenated as discussed below to reduce the substrate benzenoid rings to form the desired product, Compound 2. The individual constituents of the reaction mixture are in solution during hydrogenation and preferably prior thereto, except for the catalyst, which is heterogeneous.

The catalytic hydrogenation (reduction) is typically carried out at a pressure of about 200 psi to about 1000 psi. More preferably, that reduction is carried out at about 400 psi to about 800 psi, with about 500 psi being a most preferred pressure. One pound per square inch (psi) is about 0.069 bar (or atmospheres) and about 0.070 kg/cm$^2$. Thus, about 200 psi to about 1000 psi is about 14 to about 70 kg/cm$^2$ and about the same in bar or atmosphere units.

The catalytic hydrogenation is typically carried out at a temperature of about 35° C. to about 200° C. More preferably, that temperature is about 60° C. to about 65° C. The catalytic reduction is continued for a time sufficient to reduce at least 90 percent of the substrate, with at least 95 percent consumption being preferred and 100 percent being most preferred. These times can range from about two hours to about 24 hours, with time periods of about 8 to about 24 hours being preferred.

The time required for reduction is a factor of several variables including the temperature and pressure at which the hydrogenation is carried out. The amount of carboxylic acid or anhydride present also plays a role. Thus, in one study using a temperature of 100° C., a pressure of 1000 psi, a single catalyst of moderate activity and about 4 weight percent acetic acid, consumptions of 85, 95, 97 and 99 percents of the substrate were obtained after 2, 4, 8 and 24 hours of hydrogenation, respectively, providing a reduction product, Compound 2, having a constant D-value of about 2.6; i.e., about 43 percent of the desired isomer.

Once the hydrogenation is stopped, the temperature of the reduced, liquid reaction mixture is brought to ambient temperature, the pressure is released and brought to ambient and excess hydrogen gas is typically removed following standard practices. The heterogeneous catalyst is separated from the liquid reaction mixture as by filtration. The solvent is removed by rotary evaporation under reduced pressure, and the residue is dried under high vacuum at a temperature of about 110° to about 120° C. for about 4 to about 24 hours. Acetic acid boils at about the same temperature as n-butanol so most if not all of the carboxylic acid is removed with solvent. However, an extraction with water from a toluene solution of the redissolved reduction product can be used to remove residual carboxylic acid.

Substantially any high pressure hydrogenation apparatus can be used. One exemplary apparatus is a 4-liter Zipperclave™ of Autoclave Engineers, Erie, Pa. A Parr Reactor can also be used.

BEST MODE FOR CARRYING OUT THE INVENTION

Example 1: Standard $Sr^{+2}$ Extraction Procedure

The extraction of $HNO_3$ by various solvents to obtain D-values is measured by equilibrating an organic phase containing 0.1 molar of the 4,4'(5')-[ di-t-butyldicyclohexano]-18-crown-6 in n-octanol four times with a 1M $HNO_3$ solution using an organic to aqueous phase ratio of 3. The resultant organic phase is stripped of acid by repeated water washings and the washings titrated with standard sodium hydroxide. All distributions of $Sr^{+2}$ are measured radiometrically. Prior to a distribution study, the organic phase is preequilibrated by contacting it 2–3 times with twice its volume of 1M $HNO_3$. A 1.00 ml aliquot of this preequilibrated organic phase is then combined with an equal volume of fresh 1M $HNO_3$ spiked with $^{85}Sr^{+2}$. The two phases are mixed using a vortex mixer for one minute, then centrifuged until complete phase separation is obtained. The $^{85}Sr^{+2}$ activity in each phase is measured by gamma counting using a Beckman Biogamma Counter. All measurements are performed at 25°±0.5° C.

Example 2: Detailed Procedure for High Pressure Hydrogenation

A. Drying of Catalyst (APX-1/AP-8 (2:1)

Catalysts APX-1 and AP-8 are mixed together in a 2:1 ratio by weight. A magnetic stir bar is placed in the flask and the mixture is dried under high vacuum at about 110°–120° C. for four hours or more with stirring. A glass wool stopper is placed on the neck of the vacuum cock while the catalyst is being dried to prevent the catalyst from flowing into the vacuum pump. The flask is capped with a septum, and dry nitrogen is placed in contact with the catalyst. The catalyst sometimes loses weight during this procedure, and an unknown liquid has been observed to appear at the vacuum cock in keeping with the loss on heating indicated in the catalyst specifications.

B. Distillation of n-Butanol

About 2.3 L of n-butanol are placed in 3L-round bottom flask and heated to reflux temperature. The first about 300–350 mL of distillate are discarded and the next distillate is gathered into a 2L-round bottom flask until about 200 mL of n-butanol remain in the 3-L flask. The 2-L flask is capped with a septum and dry nitrogen from a balloon is placed in contact with the n-butanol.

C. Washing the Hydrogenation Reactor

A 2 percent NaOH solution is added to the glassware of a hydrogenation reactor of a 4-liter Zipperclave™ made by Autoclave Engineers, Erie, Pa. The upper part of the reactor is put into the glassware, the reactor is set up and stirred for 30 minutes. The upper part of the reactor is removed and washed with water and the glassware and the lower part are washed with water. Using a 2 percent HCl solution, the same procedure is repeated and the upper and lower parts and the glassware are washed with water. The same procedure is repeated using water, and the upper and lower parts and the glassware are then washed with acetone following the same procedures. The acetone-washed equipment is then permitted to dry in the air. The reactor and glassware are dried again immediately before use by use of a heat gun.

D. Drying the Substrate by Benzene-Azeotropy

The substrate is dissolved in benzene (usually about 500 mL of benzene are used for 50 grams or more sample, 250 mL for 50 grams or less). A Dean-Stark collector, a condenser, and a nitrogen sparge are set on the flask. The solution is heated to reflux temperature and the benzene-containing azeotrope collected in the Dean-Stark collector is discarded several times intermittently. The refluxing is continued for four hours or more (usually about 18 hours for a large-scale reaction). The benzene is removed by a rotary evaporator with a caution not to contact with water. When the benzene is almost removed and crystals start to form, the viscous solution is dissolved in n-butanol.

E. Hydrogenation Reaction

The substrate and some benzene that is dried and evaporated in D, above, is dissolved in n-butanol. The mixing and dissolution should be carried out as rapidly as possible to avoid possible contact with moisture in the air.

The substrate in n-butanol is transferred to the glassware of the hydrogenator, the catalyst [APX- 1/AP-8 (2:1)] and carboxylic acid or anhydride are added to the glassware on the balance to do weighing and adding at one time.

The glassware is placed on the reactor and all the parts of reactor are set up. Nitrogen is passed through a dying agent ($CaCl_2$) chamber is flushed into the reaction mixture while the reactor is heated rapidly for about ten minutes (the temperature of the reactor is about 35°–40° C. at this stage). The nitrogen tube is disconnected, all the valves are stopped, and the hydrogen is added to 500 psi. After this step, the temperature of the reactor rises rapidly. When the temperature of the reactor reaches 65° C., the heater is set to maintain a temperature of about 65° C. When the reaction occurs, the pressure drops. Hydrogen is added to maintain the pressure at about 460–540 psi for 20 hours.

F. Workup

The reactor is cooled to about 30° C. and the hydrogen is slowly removed from the reactor to a hood. When all the hydrogen goes out of the reactor, nitrogen is flushed through the reactor for about ten minutes to eliminate residual hydrogen in the reactor. The reactor is turned off and the upper part of the reactor is removed from the glassware with washing using methanol. The reaction mixture is filtered through a filter paper and again through a microfitter (Millipore). The filtrate is evaporated by use of rotary evaporator as much as possible at about 100° C. and the residue is dried under high vacuum at about 110°–120° C. for four hours or more (usually about 18 hours for a large scale reaction). The sample is less viscous when it is hot so that it can be transferred to a bottle. Although there is some loss by this type of transfer, it is quite convenient.

Example 3: Synthesis of Compound 2

A series of standardized studies was conducted in which time, temperature, pressure and catalyst were varied, whereas the solvent, n-butanol, was kept constant as were its amount and the amount of substrate. Thus, n-butanol was used at 300 ml, substrate at 10 g, with a substrate to catalyst weight ratio of 10:1. The amount and identity of acid were also varied. The amount of acid was adjusted to provide a constant 15 mmoles. The results of these studies are shown in Table 1, below.

TABLE 1

| Run | Reaction Time (h) | Reaction Temperature (°C.) | Pressure (psi) | Conversion of Compound 1 | D-Value | Acid[1,2] (%) |
|---|---|---|---|---|---|---|
| Control[3] | 22 | 100 | 1,000 | 95 | — | No |
| 1 | 25 | 100 | 100 | 10 | — | No |
| 2 | 17 | 100 | 1,500 | 14 | — | No |
| 3 | 24 | 100 | 1,000 | 94 | 2.24 | 20 |
| 4 | 24 | 100 | 500 | 95 | 2.11 | 50 |
| 5 | 24 | 80 | 500 | 100 | 2.2 | 80 |
| 6 | 24 | 60 | 500 | 100 | 1.93 | 80 |
| 7 | 24 | 60 | 200 | 100 | 2.02 | 80 |
| 8[6] | 1,2,4,8,24 | 100 | 100 | 99 | 2.56 | 40 |
| 9[4] | 24 | 60 | 200 | 95 | 2.67 | 10 |
| 10[4] | 24 | 60 | 200 | 100 | 0.86 | 20[5] |

[1] Acetic acid was present as the $C_2$–$C_6$ carboxylic acid unless so indicated by "No".
[2] The numerical value is the amount of acid expressed as a weight percentage of catalyst weight.
[3] Control - Reduction of dibenzo-18-crown-6 in place of 4,4'(5')-[di-t-butyl-dibenzo]-18-crown-6, with the conditions of Pederson, Org. Syn., Col. Vol. VI, Wiley, New York, pp. 395–400.
[4] Englehard Industries Catalyst APX-1 used in place of AP-8.
[5] Acetic acid replaced by sulfuric acid.
[6] Yields at each time were:
1 hr = 72%;
2 hr = 85%;
4 hr = 95%;
8 hr = 98%;
24 hr = 99%

Example 4: Hydrogenation with Various Acids

A series of hydrogenation reactions was carried out in which the acid or anhydride present was varied. Each reduction utilized 10 g of Compound 1, 1 g of catalyst (1:1, AXP-1:AP-8), 300 g of n-butanol, a hydrogen pressure of 500 psi, a hydrogenation temperature of 60° C. and a reduction time of 12 hours. Each acid or anhydride was used at 15 mmolar. The results of this study are shown in Table 2, below.

TABLE 2

| Carboxylic Acid | Substrate Consumption[1] (%) | Product D-Value |
|---|---|---|
| Formic[2] | 5 | — |
| Acetic | 100 | 4.4 |
| Acetic Acid/Acetic Anhydride (1:1) | 95 | 4.2 |
| Propionic[3] | 53 | 1.5 |
| Butyric | 86 | 3.5 |
| Isobutyric | 66 | 3.0 |
| Valeric | 69 | 3.0 |
| Isovaleric | 100 | 4.2 |
| Neopentanoic | 37 | 0.6 |
| p-toluenesulfonic | 0 | — |

[1] Substrate consumption was assessed by the change in integrated area for aromatic protons relative to the other protons observed in $^1$H-NMR.
[2] Formic acid sublimed from the reaction vessel.
[3] The reason for the observed low conversion percentage and poor D-value are unknown, and the result appears to be anomalous.

Example 5: Hydrogenation with Various Ratios of Catalysts

A series of hydrogenation was carried out using one or the other or both of catalysts AXP-1 and AP-8. Each reduction utilized 10 g of Compound 1, 1 g of total catalyst, 300 ml of n-butanol, a hydrogen pressure of 500 psi, a hydrogenation temperature of 55°–65° C. and a reduction time of 20 hours. An amount of glacial acetic acid equal in weight to the total catalyst weight was used. The results of this study are shown in Table 3, below.

TABLE 3

| Parts by Weight | | D-Value |
|---|---|---|
| APX-1 | AP-8 | |
| 1 | 0 | 3.5 |
| 13 | 1 | 3.2 |
| 9 | 1 | 3.9 |
| 2 | 1 | 4.2–4.6 |
| 0 | 1 | 4.5 |
| 1 | 10 | 4.7 |
| 1 | 30 | 4.5 |
| 1 | 45 | 5.0 |

It is seen from the above results that use of either catalyst alone provides good results. The most consistently good results are provided by the 2:1 weight ratio catalyst.

Example 6: Synthesis of Compound 2 Containing More Than 50 Percent Compound 2b Three separate catalytic hydrogenations were carried out using a reaction temperature of 65° C., a pressure of 500 psi and a reaction time of 20 hours. The catalyst in each case was a mixture of highly active and moderately active catalysts APX-1 and AP-8, respectively, at a weight ratio of 2:1. Reduction run A was carried out using 8 g of the combined catalyst, whereas runs B and C were each carried out using 15 g of that catalyst. Acetic acid was used as the $C_2$–$C_6$ carboxylic acid, and was present at the same weight as the catalyst. The results are shown in Table 4, below.

TABLE 4

| Reduction Run | Compound 1 (grams) | n-Butanol (ml) | Product Yield (%) | D-Value |
|---|---|---|---|---|
| A | 77.2 | 500 | 97 | 4.2 |
| B | 152.0 | 800 | 99 | 4.2 |
| C | 152.0 | 800 | 99 | 4.1 |

As can be seen from the above data, extremely high conversions of purified Compound 1 to Compound 2 were obtained using conditions much more moderate than those of the literature for reducing the dibenzo-18-crown-6. It is also seen that these conditions produced relatively large amounts of the desired Compound 2 isomer (about 70 percent) based on the D-values. The Compound 2 so prepared can be dissolved in n-octanol and utilized as discussed in U.S. Pat. Nos. 5,100,585, 5,110,474 or 5,346,618 without further purification.

Example 7: Further Synthesis of Compound 2 Containing More than 50 Percent Compound 2b Purified Compound 1 (50 g) dissolved in 231 g toluene was heated to reflux to azeotropically dry the substrate. Of the original toluene present, 110 g were distilled off to provide 50 g of substrate dissolved in 121 g of dry toluene. To that solution were added 5 g of dried catalyst (APX-1:AP-8=2:1 by weight), 351 g of distilled n-butanol and 4.8 ml (5.04 g) of glacial acetic acid to form a reaction mixture. That reaction mixture was hydrogenated at 65° C., 500 psi for 20 hours to provide complete reduction of the substrate.

After cooling the hydrogenated reaction mixture, and removing excess hydrogen gas, the reaction vessel was flushed with nitrogen gas for ten minutes. The hydrogenated reaction mixture is filtered to remove the catalyst, and the solvent was removed from the filtrate under reduced pressure at a temperature of about 100° C. The dried product is redissolved in 100 ml of toluene, and extracted with two 100 ml portions of water to remove residual acetic acid. The toluene solution was thereafter dried on a rotary evaporator under reduced pressure and at about 100° C. The resultant material was dried under high vacuum for several hours. The D-value of this product was 4.6, with a recovered yield of only 65 percent due to transfer losses.

A similar preparation was made using 100 g of purified Compound 1 initially dissolved in 500 g of toluene. Azeotropy and distillation provided 100 g of purified, dry Compound 1 dissolved in 230 g of dry toluene to which 10 g of dried catalyst, 250 g dried butanol and 9 ml (9.5 g) glacial acetic acid were added. Hydrogenation as before followed by the previously discussed workup using 200 ml portions of water for extractions, provided a recovered yield of Compound 2 of 87 percent. That material had a D-value of 4.4.

The products prepared in this example can also be utilized without further purification.

The foregoing description and the examples are intended as illustrative and are not to be taken as limiting. Still other variations within the spirit and scope of this invention are possible and will readily present themselves to those skilled in the art.

We claim:

1. A process for forming a 4,4'(5')-[ di-t-butyldicyclohexano]-18-crown-6 product containing at least one-third cis-syn-cis isomer that comprises the steps of:
   (a) forming an anhydrous reaction mixture that consists essentially of 4,4'(5')-[ di-t-butyldibenzo]-18-crown-6 as substrate dissolved in a solvent that is a $C_2$–$C_6$ alkyl alcohol containing zero to 2 parts by weight benzene, toluene or xylene per part alcohol, a reduced, dry catalyst that contains about 5 weight percent of rhodium on alumina particles and a $C_2$–$C_6$ carboxylic acid or $C_2$–$C_6$ carboxylic anhydride, said substrate being free of oxyethylene hydroxylic and oxyethylene phenolic impurities, the weight ratio of said substrate to said catalyst being about 50 to about 5:1, and the weight ratio of said catalyst to said $C_2$–$C_6$ carboxylic acid or anhydride being about 0.5:1 to about 10:1; and
   (b) hydrogenating said reaction mixture at a pressure of about 200 to about 1000 psi at a temperature of about 35° to about 120° C. for a time period sufficient to reduce at least 90 percent of said substrate.

2. The process according to claim 1 wherein said $C_2$–$C_6$ alkyl alcohol is n-butanol.

3. The process according to claim 1 wherein said catalyst is a mixture having alumina particles of BET surface area of about 115 $m^2$/g and about 110 $m^2$/g.

4. The process according to claim 3 wherein said catalyst is a mixture of about two parts of alumina particles of about 115 $m^2$/g and one part of alumina particles of about 110 $m^2$/g.

5. The process according to claim 1 wherein said pressure is about 400 to about 800 psi.

6. The process according to claim 2 wherein said temperature is about 60° to about 65° C.

7. The process according to claim 1 wherein said time period is about 2 to about 24 hours.

8. The process according to claim 1 wherein said $C_2$–$C_6$ carboxylic acid or anhydride is acetic acid or acetic anhydride.

9. The process according to claim 1 wherein said product contains at least one-half cis-syn-cis isomer.

10. The process according to claim 1 wherein the weight ratio of said substrate to said catalyst is about 20 to about 10:1, and the weight ratio of said catalyst to said carboxylic acid or anhydride is about 1:1.

11. A process for forming 4,4'(5')-[ di-t-butyldicyclohexano]-18-crown-6 product containing at least one-half cis-syn-cis isomer that comprises the steps of:
   (a) forming an anhydrous reaction mixture that consists essentially of 4,4'(5')-[ di-t-butyldibenzo]-18-crown-6 as substrate dissolved in n-butanol and benzene or toluene in which n-butanol is about three-fourths to about one-half the solvent, a reduced, dry catalyst that contains about 5 weight percent of rhodium on alumina particles, said catalyst being a mixture of about two parts alumina particles having a BET surface area of about 115 $m^2$/g and one part having a BET surface area of about 110 $m^2$/g, and acetic acid or acetic anhydride, said substrate being free of oxyethylene hydroxylic and oxyethylene phenolic impurities, the weight ratio of said substrate to said catalyst being about 20 to about 10:1 and the weight ratio of said carboxylic acid or anhydride to said catalyst being about 1:1; and
   (b) hydrogenating said reaction mixture at a pressure of about 400 to about 800 psi at a temperature of about 60° to about 65° C. for a time period of about 2 to about 24 hours.

* * * * *